(12) United States Patent
Barry et al.

(10) Patent No.: US 7,233,838 B2
(45) Date of Patent: Jun. 19, 2007

(54) TRANSFER AND POSITIONING APPARATUS FOR AUTOMATED CONVEYOR SYSTEM

(75) Inventors: Douglas Barry, Lincoln, NE (US); Thomas L. Bybee, Omaha, NE (US); Adrian Chan, Richmond Hill (CA); John Fuller, Omaha, NE (US); Ray Puseman, Bellevue, NE (US); Greg Rothman, Omaha, NE (US); Don R. Simms, Council Bluffs, IA (US); Michael Turner, Bellevue, NE (US); Jay Woods, Omaha, NE (US); Inna M. Zevakina, Omaha, NE (US)

(73) Assignee: Abbott Laboratories, Abbott Park, IL (US)

( * ) Notice: Subject to any disclaimer, the term of this patent is extended or adjusted under 35 U.S.C. 154(b) by 805 days.

(21) Appl. No.: 10/627,342

(22) Filed: Jul. 25, 2003
(Under 37 CFR 1.47)

(65) Prior Publication Data
US 2004/0096362 A1 May 20, 2004

Related U.S. Application Data

(60) Provisional application No. 60/398,893, filed on Jul. 26, 2002.

(51) Int. Cl.
*G06F 7/00* (2006.01)

(52) U.S. Cl. .............. 700/213; 198/468.11; 198/468.2; 198/346.1

(58) Field of Classification Search ................ 700/213; 198/468.01, 468.2, 468.9, 459.5, 346.2, 456, 198/458, 597, 465.1, 570, 345.3, 346.1
See application file for complete search history.

(56) References Cited

U.S. PATENT DOCUMENTS 1,726,657 A * 9/1929 Ekvall ..................... 198/468.2

(Continued)

*Primary Examiner*—Douglas Hess
(74) *Attorney, Agent, or Firm*—David L. Weinstein

(57) ABSTRACT

A transfer and positioning apparatus includes a positioning assembly located between the tracks of a dual lane conveyor and upstream of a lane changer. The positioning assembly includes a retractable shaft for stopping a carrier along a first conveyor adjacent the assembly. A pair of gripper arms are pivotally mounted to move between an open position permitting the carrier to pass along the conveyor track, and a closed position with forward ends in contact with a specimen container on the carrier to position the container in a reference location for direct processing. The lane changer includes a shuttle depending from an overhead support with a pair of arms for receiving and shifting a specimen carrier from one conveyor to a second conveyor of a dual-conveyor track. The shuttle is operable to retain a specimen carrier along either the first or second conveyor and to release a specimen carrier along either the first or second conveyor. Sensors are located to detect the presence of a specimen carrier at each of the retention locations, and to confirm the release of a specimen carrier from the shuttle along each of the conveyors. A queue is positioned upstream of the positioning assembly and includes retractable shafts, sensors and scanners for selectively retaining, detecting and scanning identification data from a specimen carrier on either conveyor upstream of the shuttle.

18 Claims, 10 Drawing Sheets

U.S. PATENT DOCUMENTS

| | | | | |
|---|---|---|---|---|
| 2,451,104 | A * | 10/1948 | Lowe | 198/442 |
| 3,160,259 | A * | 12/1964 | Dalton | 198/432 |
| 4,809,839 | A * | 3/1989 | Elliott | 198/766 |
| 5,228,551 | A * | 7/1993 | Kluttermann et al. | 198/468.11 |
| 6,328,153 | B1 * | 12/2001 | Manghi et al. | 198/736 |
| 6,435,336 | B1 * | 8/2002 | Knodler | 198/474.1 |
| 6,574,528 | B1 * | 6/2003 | Toya et al. | 700/213 |
| 6,853,876 | B2 * | 2/2005 | Wehrung et al. | 700/230 |
| 6,893,120 | B2 * | 5/2005 | Bailey et al. | 347/87 |
| 6,999,847 | B2 * | 2/2006 | Barry et al. | 700/123 |

* cited by examiner

TRANSFER AND POSITIONING APPARATUS FOR AUTOMATED CONVEYOR SYSTEM

CROSS-REFERENCES TO RELATED APPLICATIONS

This application claims the benefit of U.S. Provisional Application Ser. No. 60/398,893, filed Jul. 26, 2002.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to a specimen carrier transfer apparatus for transferring specimen carriers from one conveyor to another in a dual conveyor system, and more particularly to an improved transfer apparatus with specimen positioning capabilities.

(2) Background Information

Clinical laboratory testing has changed and improved remarkably over the past 80 years. Initially, tests or assays were performed manually and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of physical specimen required to perform a particular test.

Instruments have been developed to increase the efficiency of testing procedures by reducing turnaround time and decreasing the volumes necessary to perform various assays. Robotic engineering has evolved to such a degree that various types of robots have been applied in the clinical laboratory setting.

The main focus of prior art laboratory automation relied on the implementation of conveyor systems to connect areas of a clinical laboratory. Known conveyor systems in the laboratory setting utilize separate conveyor segments to move specimens from a processing station to a specific laboratory work station. In order to obtain cost savings, one typical scenario called for specimens to be sorted manually and grouped together in a carrier rack to be conveyed to a specific location. In this way, a carrier would move a group of 5–20 specimens from the processing location to the specific work station for the performance of a single test on each of the specimens within the carrier rack.

With the development of new and improved automatic conveyor systems for laboratories and other environments, it is possible to select, track, and convey individual specimens throughout a laboratory for a variety of different testing, while maintaining a priority system for certain types of testing or special urgent requests for a time-specific response. These new automated conveyor systems are of various types and design, but the inventors herein have found that a dual conveyor system, using a pair of parallel conveyor tracks circulating throughout a laboratory, provides the greatest flexibility and versatility. The integration of various track devices with software directing the operation of the conveyor system and the various automated testing stations, has improved both the speed and capability of automated conveyor systems in recent years.

Track devices form the physical interface between the specimen samples in carriers being directed throughout the system, while the Laboratory Automation System (LAS) database provides direction for the system through its command and control features. The LAS and the various track devices work in combination to direct, manage and track all specimens throughout the system.

The dual-lane conveyors used in the present invention utilize table top chain to transport specimen carriers about a closed loop, among various stations. Typically, the inside lane of the dual lane conveyor acts as a highway to rapidly transport specimens to their proper destination. The outside lane accepts specimens diverted to it from the inside lane, and queues them for processing at one of the automation system modules or laboratory instruments. The continuous loop dual lane design means that specimens will quickly circulate back to any module or instrument on the system without operator intervention. Rules based processing guidelines determine all specimen actions, including routing changes for additional testing or modified processing.

In order to effectively manage, track and route specimens throughout a clinical laboratory, it is necessary to maintain constant "awareness" of the location of every specimen throughout the system, and be able to direct each specimen to the appropriate location at the most appropriate time for storage, testing or other processing. This in turn is accomplished, in part, by one or more transfer apparatus for selectively shifting a specimen carrier between the inside and outside lanes of the dual lane conveyor.

It is desirable to provide repeatable sample positioning along the conveyor system, so that a sample tube within a specimen carrier is repeatedly located at a fixed point along the track for direct specimen tube operations. While the transfer apparatus of the applicants' co-pending patent application provides the tracking, identification and direction desired for a specimen carrier within the conveyor track system, it does not provide for the more particularized capability of positioning a specimen tube carried by a carrier in a repeatable location to permit such processing.

BRIEF SUMMARY OF THE INVENTION

It is therefore a general object of the present invention to provide an improved transfer apparatus with specimen positioning capabilities.

A further object is to provide a transfer apparatus with the ability to repeatably position a specimen tube within a specimen carrier in a predetermined location.

These and other objects will be apparent to those skilled in the art.

The transfer and positioning apparatus of the present invention includes a positioning assembly located between the tracks of a dual lane conveyor and upstream of a lane changer. The positioning assembly includes a retractable shaft for stopping a carrier along a first conveyor adjacent the assembly. A pair of gripper arms are pivotally mounted to move between an open position permitting the carrier to pass along the conveyor track, and a closed position with forward ends in contact with the a specimen container on the carrier to position the container in a reference location for direct processing. The lane changer includes a shuttle depending from an overhead support with a pair of arms for receiving and shifting a specimen carrier from one conveyor to a second conveyor of a dual-conveyor track. The shuttle is operable to retain a specimen carrier along either the first or second conveyor and to release a specimen carrier along either the first or second conveyor. Sensors are located to detect the presence of a specimen carrier at each of the retention locations, and to confirm the release of a specimen carrier from the shuttle along each of the conveyors. A queue is positioned upstream of the positioning assembly and includes retractable shafts, sensors and scanners for selectively retaining, detecting and scanning identification data from a specimen carrier on either conveyor upstream of the shuttle.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which.

DETAILED DESCRIPTION OF THE INVENTION

Figure 1:
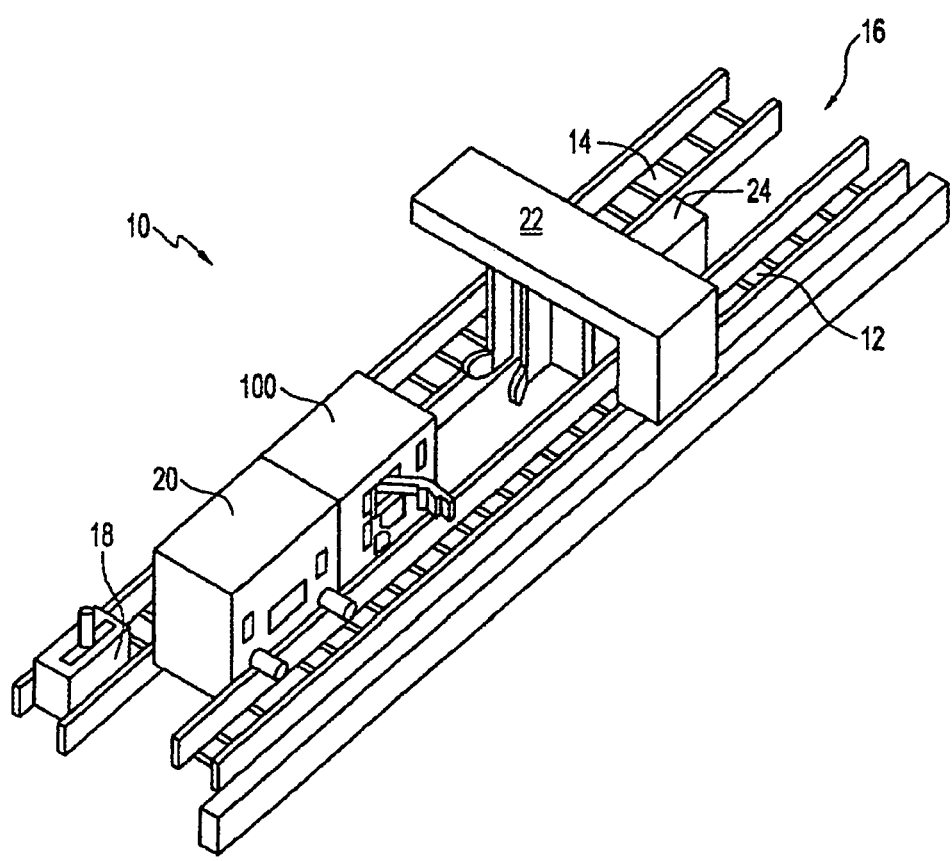
FIG. 1 is a perspective view of a transfer and positioning apparatus of the present invention installed along a dual lane conveyor track.

Referring now to the drawings, in which similar or corresponding parts are identified with the same reference numeral, and more particularly to FIG. 1, the transfer apparatus of the present invention is designated generally at 10, and is shown installed between two conveyors 12 and 14 of a dual lane automated conveyor transport track 16, to selectively transfer a specimen carrier 18 between conveyors 12 and 14. Transfer apparatus 10 includes four general components: a queue 20, a lane changer 22, a command module 24 and a positioning assembly 100. Queue 20 serves to stop each specimen carrier 18 that travels by the queue, identify the carrier 18 and then release the carrier at a time determined by the command module 24. Positioning assembly 100 serves to stop a carrier with a projecting test tube at a predetermined position so that direct processing of the sample within the tube may be performed. Positioning assembly 100 is operated by the command module 24. Lane changer 22 is operated by the command module 24 to receive and shift a specimen carrier 18 from one of conveyors 12 or 14, to the other. The command module 24 serves as the "brain" of the transfer apparatus 10 and interacts with the Laboratory Automation System (LAS) to identify, track and direct specimen carriers 18 through the transfer apparatus 10.

Figure 2:
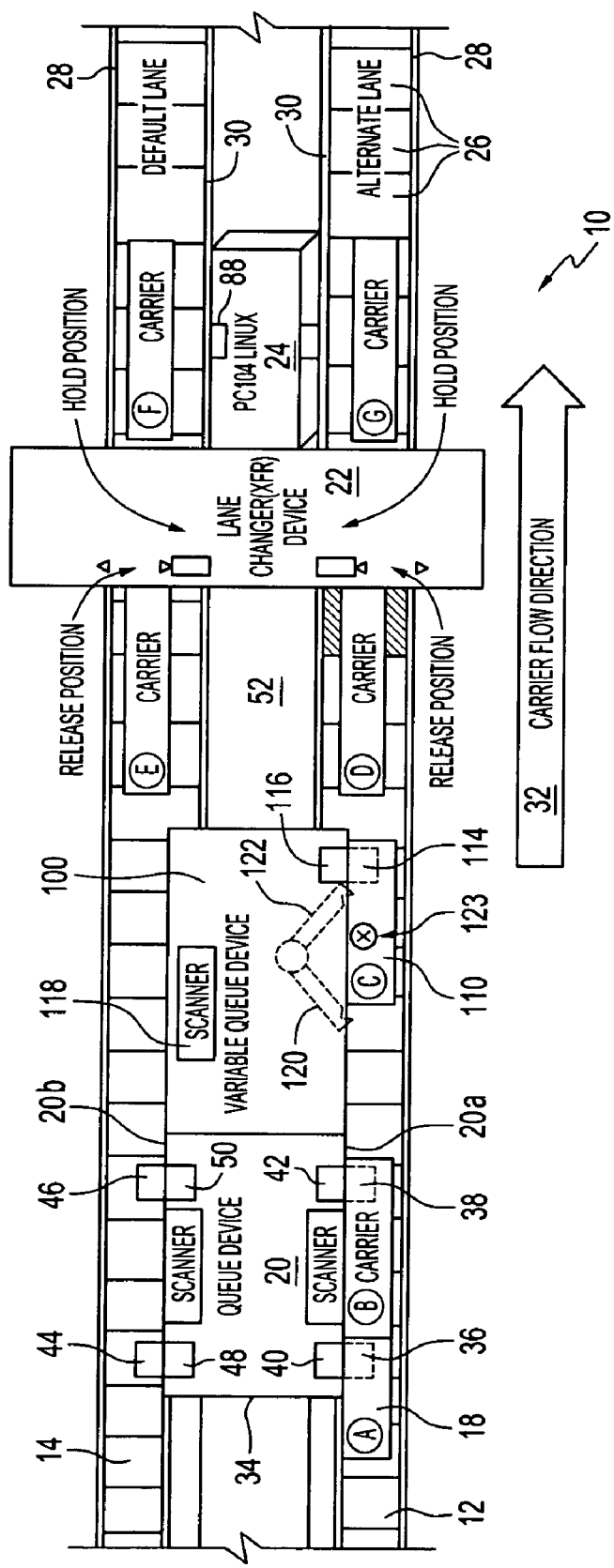
FIG. 2 is a top plan view of the transfer and positioning apparatus, showing various possible positions of a specimen carrier as the transfer apparatus operates.

Referring now to FIG. 2, conveyors 12 and 14 use a table top chain known in the art to transport specimen carriers 18. Each table top chain includes a plurality of plates 26, each having a flat upper surface or "table top" for moving carriers 18. Plates 26 are interconnected by links, which permit plates 26 to pivot about the links within a horizontal plane. The links are engaged by a drive mechanism to pull the chain along track 16 and thereby move carriers 18 supported on the track. The upper surfaces of plates 26 form a flat planar surface identified throughout this specification as a drive plane.

A pair of elongated guide rails 28 and 30 are disposed along the lengths of each conveyor 12 and 14 on opposing sides of plates 26 to guide specimen carriers 18 therebetween. One embodiment of specimen carriers 18 is disclosed throughout this specification, but it should be understood that many other sizes and shapes of carriers for specimens could be utilized with the present invention. Each specimen carrier 18 includes a generally rectangular body with a forward wall and a top surface. A plurality of openings are formed in the top surface and extend into the interior of the body for receiving and supporting a specimen tube, slide, or other specimen container in an upright position.

Conveyors 12 and 14 operate in the same direction, designated generally by arrow 32, although they may be operated at different speeds. Queue 20 includes a housing 34 positioned between conveyors 12 and 14 and located upstream of lane changer 22. A pair of forward and rearward retractable shafts 36 and 38 extend transversely outwardly from a first side 20a of queue 20, and project over conveyor 12 to restrain a specimen carrier 18 from passing by shaft 36 or 38. Forward and rearward sensors 40 and 42 are positioned adjacent each shaft 36 and 38, respectively, to detect the presence of a specimen carrier 18 at the associated shaft.

A second pair of forward and rearward retractable shafts 44 and 46 extend transversely outwardly from the opposing second side 20b of queue 20, and project over conveyor 14 to restrain a specimen carrier 18 from passing by shaft 44 or 46. Forward and rearward sensors 48 and 50 are positioned adjacent each shaft 44 and 46, respectively, to detect the presence of a specimen carrier 18 at the associated shaft.

In the preferred embodiment of the invention, forward shafts 36 and 44 are the projecting ends of a single shaft. In this way, only one carrier 18 is permitted to continue downstream at a time, since the retraction of one end of the shaft would cause the other end to project farther over the opposing track. Similarly, rearward shafts 38 and 46 are preferably the projecting ends of a second single shaft. Again, only one carrier is permitted to advance downstream from queue 20 along the conveyors 12 and 14.

The inward guide rails 30 of conveyors 12 and 14 are removed from between the downstream end of queue 20 and lane changer 22, and a platform 52 is installed with its top surface coplanar with the drive plane of conveyors 12 and 14. Thus, carriers 18 may be moved off of one conveyor and onto the other by sliding the carrier across platform 52.

Figure 3:
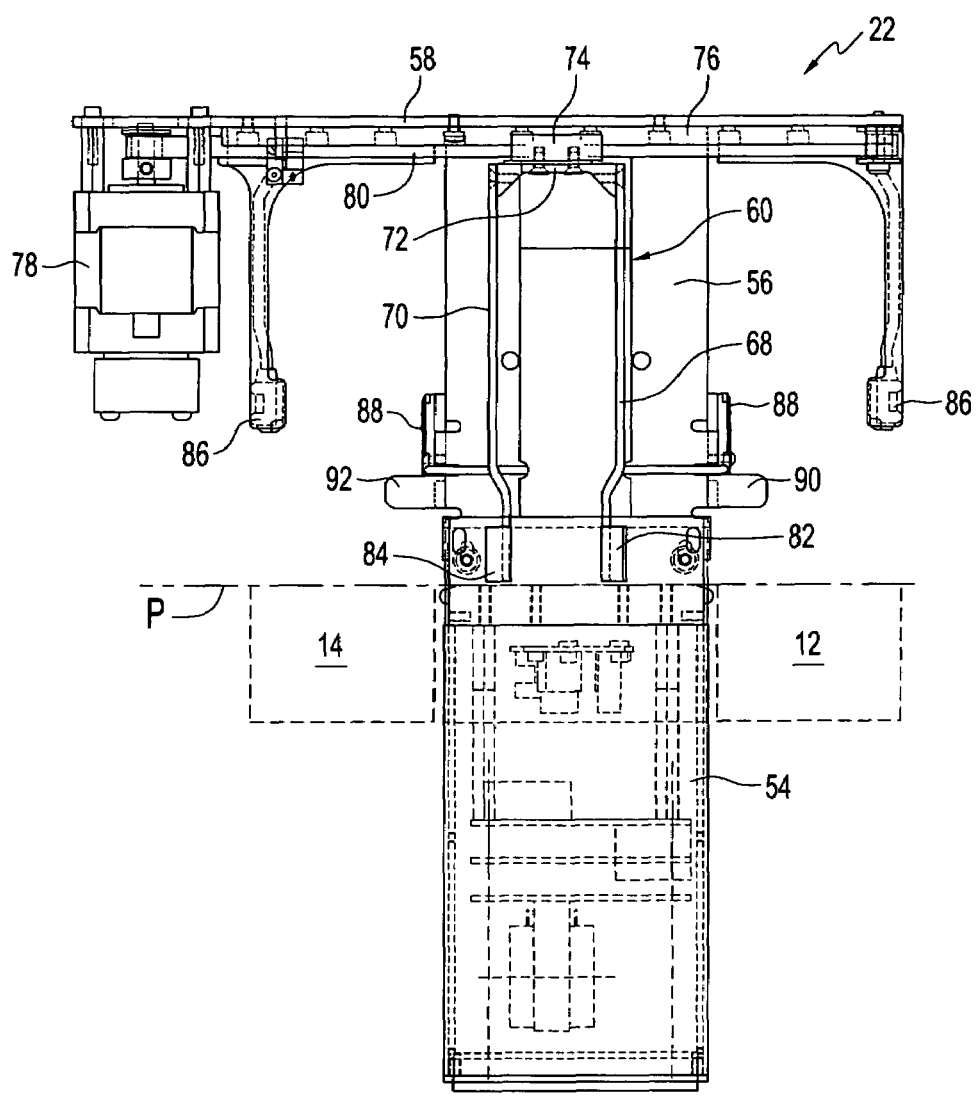
FIG. 3 is a front elevational view of the lane changer of the invention.
Figure 4:
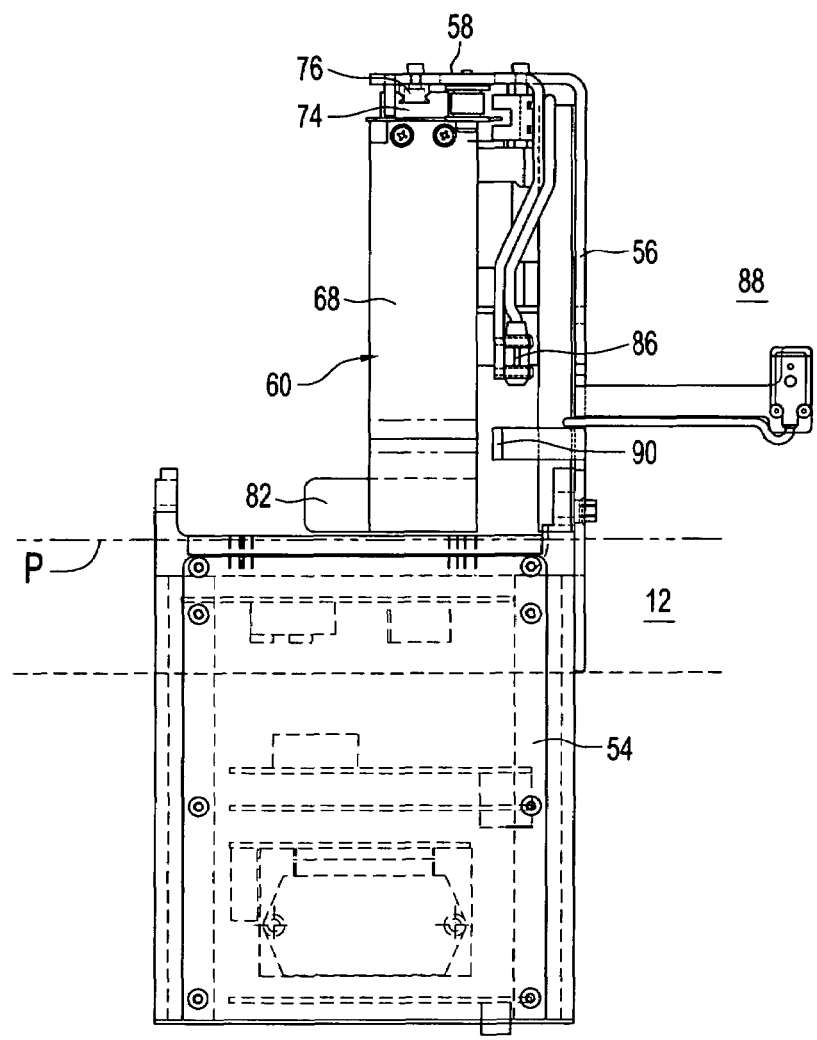
FIG. 4 is a side elevational view of the lane changer.
Figure 5:
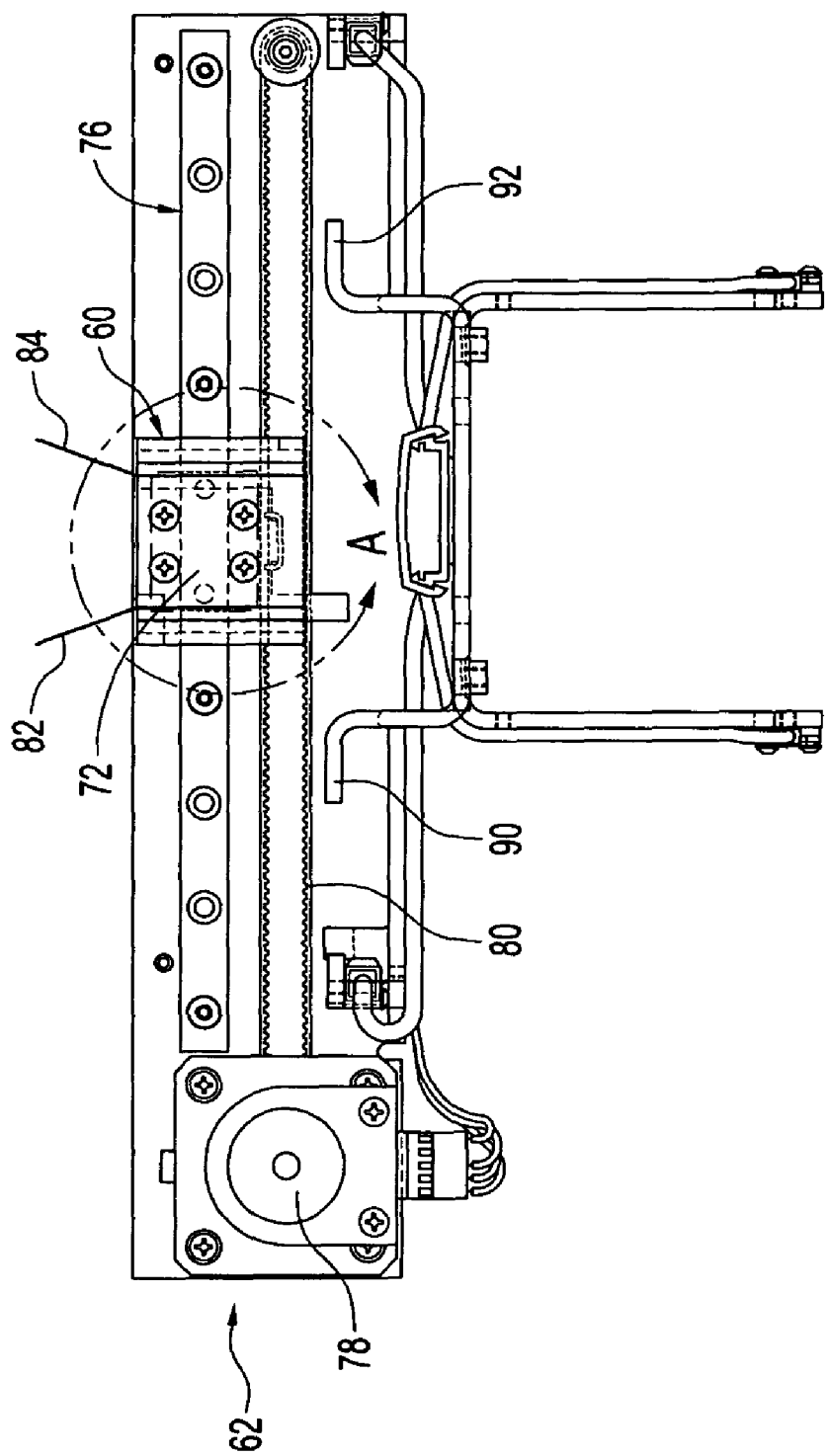
FIG. 5 is a bottom view of the drive assembly of the lane changer.

As shown in FIGS. 3 and 4, lane changer 22 includes a lower housing 54 mounted between conveyors 12 and 14 and depending below the drive plane "P". A rigid upright back 56 is connected at its lower end to housing 54 and projects upwardly between conveyors 12 and 14. A support plate 58 projects forwardly and transversely outwardly from the top of back 56, and serves as the frame for supporting the shuttle 60, the shuttle drive assembly 62 and sensors 64 and 66, all of which are described in more detail hereinbelow.

Shuttle 60 serves to receive a specimen carrier 18 between a pair of arms 68 and 70 and transversely move carrier 18 between conveyors 12 and 14, and includes a base plate 72 connecting the upper ends of arms 68 and 70 to form an inverted U-shaped structure. Base plate 72 is mounted to the bottom of a slide 74 which in turn is slidably connected to a linear rail 76 on the bottom of support plate 58. As shown in FIG. 3, linear rail 76 extends transversely over both conveyors 12 and 14, thereby permitting movement of shuttle 60 over both conveyors. An encoder-monitored DC stepper motor 78 selectively drives a drive belt 80 connected to slide 74 to precisely position shuttle 60 where desired along rail 76.

The lower ends of arms 68 and 70 on shuttle 60 each have a guide blade 82 and 84, respectively, mounted thereon. Blades 82 and 84 diverge outwardly as they project forwardly from the arms 68 and 70, to thereby shift a specimen carrier 18 transversely into alignment between the arms 68 and 70. Blades 82 and 84 are preferably formed of a resilient and flexible material so that shuttle 60 can shift fully against the outside guide rails 28 (see FIG. 2) to release a carrier 18 onto either conveyor 12 or 14.

A presence sensor 86 is positioned adjacent each outward extent of shuttle 60 to detect the presence of a carrier 18 within shuttle 60 on either conveyor 12 or 14. An exit sensor 88 is positioned downstream of shuttle 60 along each conveyor 12 and 14, to detect the presence of a carrier that has exited the shuttle along either conveyor.

A pair of carrier stop arms 90 and 92 project transversely outwardly from back 56 and extend partially over conveyors 12 and 14, respectively. However, stop arms 90 and 92 do not project far enough to prevent a carrier 18 from passing between the stop arm and the associated outside guide rail 28, if aligned with the opening therebetween by carrier shuttle 60.

Figure 6:
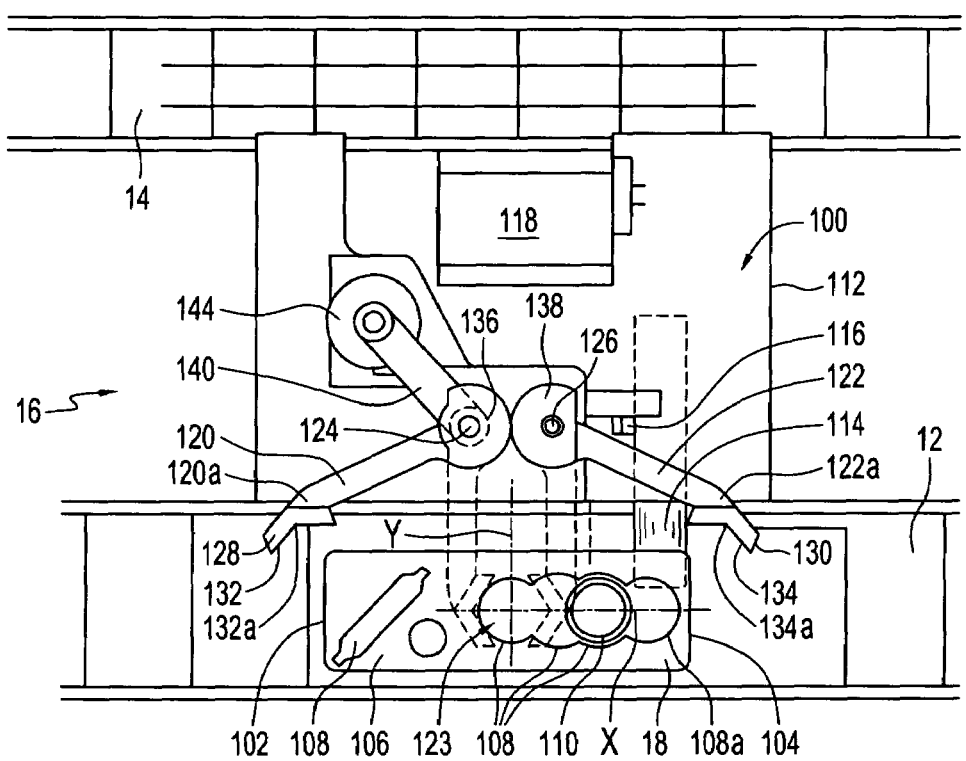
FIG. 6 is a plan view of the positioning assembly, in an open position.

Referring now to FIG. 6, specimen carrier 18 includes a generally rectangular body 102 with a forward wall 104 and a top surface 106. A plurality of openings 108 are formed in top surface 106 and extend down into the interior of body 102, for supporting a specimen container 110 in an upright orientation with an upper end projecting above the top surface of carrier 18. As shown in the drawings, openings 108 may be of various diameters and shapes, may be separated or overlapping, and may be of various depths, to provide for specimen containers of a wide variety of shapes and sizes.

Figure 7:
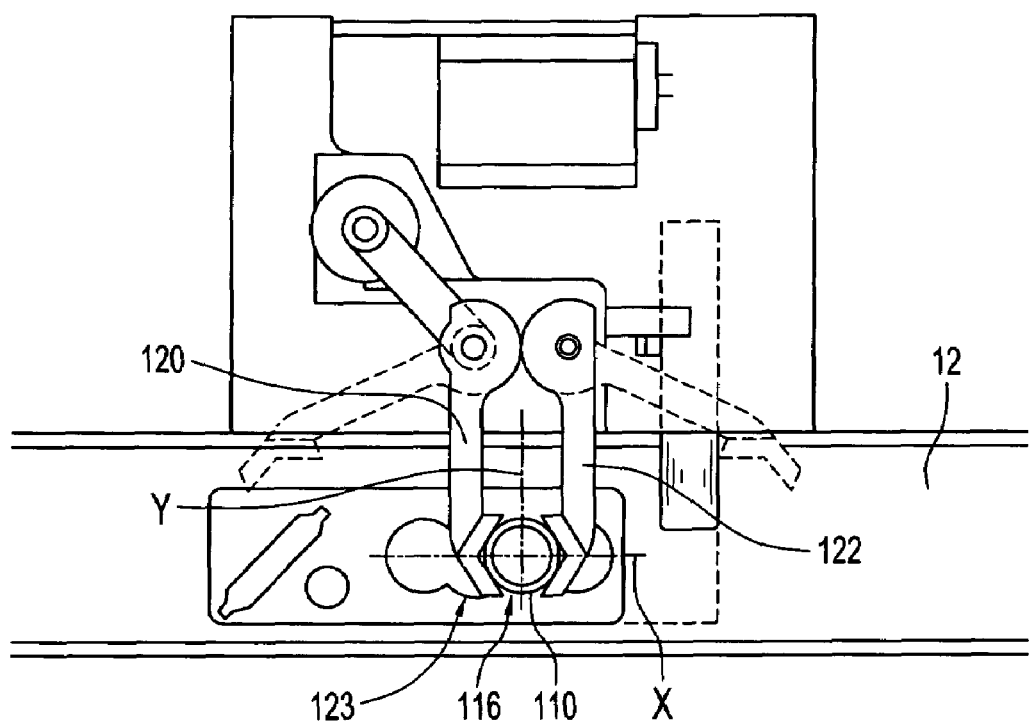
FIG. 7 is a plan view of the positioning assembly, in a closed position.

For clarity, the upstream queue 20 and the downstream lane changer 22 have been omitted from FIGS. 6 and 7. Positioning assembly 100 includes a housing 112 mounted between conveyors 12 and 14 on track 16. A retractable pin 114 is operably mounted on the forward face of housing 112, and is operable to extend over conveyor 12 a sufficient distance to contact a specimen carrier 18 and prevent downstream movement of the specimen carrier 18. A sensor 116 adjacent pin 114 detects the presence of carrier 18 and transmits the detection information to the command module 24.

In response to the detection of a carrier 18, a bar code scanner 118 will scan the bar code label on the side of carrier 18 and transmit the identification data collected to the command module 24. If carrier 18 has a specimen tube 110 with a sample to be directly processed at the positioning assembly 100, then the command module will transmit instructions to the positioning assembly 100 to engage its gripper arms 120 and 122, to grip and position the desired specimen tube 110 at a predetermined processing location, identified generally at 123.

Gripper arms 120 and 122 are pivotally mounted at rearward ends on pivot pins 124 and 126, respectively, for pivotal movement within a horizontal plane between an open position, shown in FIG. 6, and a closed/locating position, shown in FIG. 7. The forward ends 120a and 122a of arms 120 and 122 have pads 128 and 130 mounted thereon with a contact surface 132 and 134, respectively. Contact surfaces 132 and 134 are preferably "V"-shaped when viewed from above, with a pair of surfaces sloped rearwardly and inwardly towards the arms 120 and 122 to form valleys 132a and 134a. Valleys 132a and 134a are oriented vertically and aligned along the longitudinal axis X of conveyor 12, when the arms are in the closed position shown in FIG. 7. In this way, specimen tubes 110 of various sizes and diameters will be centered at a specific location along the X axis of conveyor 12 upon closing of arms 120 and 122.

As shown in FIG. 6, arms 120 and 122 pivot outwardly a sufficient distance so that the forward ends 120a and 122a of the arms are clear of specimen containers 110 in carriers 18, when in the open position. Gripper arms 120 and 122 must have a length, and are positioned such that contact surfaces 134 of pad 130 will reach and contact a specimen tube 110 located in the forward most opening 108a of a specimen carrier 18.

Positioning assembly 100 is mounted on track 16 adjacent conveyor 12 such that gripper arms 120 and 122 will position a specimen tube 110 of a carrier 18 at predetermined processing position 123. A transverse Y axis, perpendicular to the longitudinal X axis of conveyor 12, and passing though position 123, is located midway between gripper arms 120 and 122 and pivot pins 124 and 126, to accurately position the specimen tube 110 at position 123, for processing by a separate clinical instrument (not shown).

The rearward ends 120b and 122b of arms 120 and 122 have pinion gears 136 and 138, respectively, rotatably mounted on pivot pins 124 and 126, with the teeth of the gears intermeshing. Thus, pivotal movement of arm 120 on pin 124 will rotate pinion gear 136, which rotates pinion gear 138 to thereby pivot arm 122 in the opposite direction. A drive belt 140 interconnects a drive gear 142 mounted to pinion gear 136, with a reversible motor 144, to selective operate the gripper arms between the open and closed positions. Motor 144 is electrically connected to the command module 24 (shown in FIG. 1), to receive operating instructions. Although the preferred embodiment of the invention utilizes a reversible motor and belt to selectively operate gripper arms 120 and 122, it should be understood that there are a wide variety of equivalent apparatus which may be utilized to obtain the desired pivotal movement of gripper arms 120 and 122. In addition, it is possible to obtain the positioning of the specimen tube 110 at position 123 using only the downstream gripper arm 122, although such an arrangement is not preferred.

In operation, the processor of command module 124 communicates with the LAS to receive information relative to all specimen carriers 18 on the conveyors 12 and 14 of track 16. This information will determine particular specimen tubes 110 that require a stop at position 123 for processing by a clinical instrument. To position a specimen tube 110, a carrier 18 will be stopped by shaft 114 on conveyor 12. Depending upon which of the openings 108 of carrier 18 the tube 110 is located in, the tube 110 will be located either downstream of position 123, or at the desired location along the X axis of position 123, as shown in FIG. 6.

As gripper arms 120 and 122 move from the open position of FIG. 6, to the closed position of FIG. 7, the downstream arm 122 will pivot in an upstream direction, with the contact surface 134 contacting and pushing specimen tube 110 upstream to position 123. The valleys 132a and 134a of contact surfaces 132 and 134 will repeatedly position specimen tube 110 along both the X and Y axes of position 123. Because gripper arms 120 and 122 will repeatedly locate a specimen tube 110 at the exact location of position 123, it is not necessary to provide additional sensors to verify the presence or position of the tube.

Referring once again to FIG. 2, the operation of transfer apparatus 10 is as follows. While specimen carriers 18 travel along both conveyors 12 and 14 during operation the description of the operation of the transfer apparatus will assume that a carrier 18 first reaches queue 20 along conveyor 12. The rest position of all four shafts 36, 38, 44 and 46 of queue 20 are in an extended position, so that a carrier 18 is prevented from advancing beyond the associated shaft until the particular shaft is retracted. Thus, carrier 18, on conveyor 12 will first contact extended shaft 36 and stop in position "A". Sensor 40 detects the presence of carrier 18, and retracts shaft 36 to permit the carrier to proceed downstream. Carrier 18 is then stopped by extended shaft 38. When rearward sensor 42 detects the presence of carrier 18 at position "B", a barcode scanner 94 is turned on to scan the barcode label on the side of carrier 18. This data is then transmitted to the command module 24, which will determine the appropriate action to take, based upon priority rules and guidelines set up by the LAS.

Once the command module has determined the action to be taken, shaft 42 is retracted, and carrier 18 proceeds downstream. If the action to be taken requires direct processing of a sample in a specimen tube on the carrier, the command module processor will direct the shaft 114 on positioning assembly to remain in the extended position to stop carrier 18 at position "C" on conveyor 12. After sensor 116 has detected the presence of carrier 118, scanner 118 is operated to provide and confirm specific identification data to command module 24. If the specimen is the desired sample to be processed, the command module processor will instruct the gripper arms 120 and 122 to close and position the specimen tube 110 of the carrier at position 123. Once the processing of the specimen has been completed, instructions from the command module 24 will direct the gripper arms 120 and 122 to open and release the carrier to its position against shaft 114 on positioning assembly 100.

Figure 8:
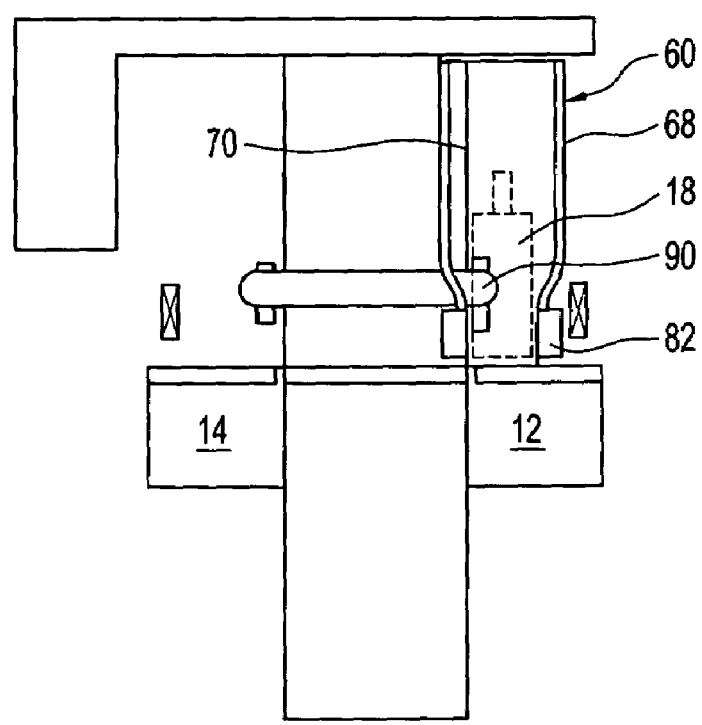
FIG. 8 is a front elevational view of the lane changer showing the shuttle in a first position.
Figure 9:
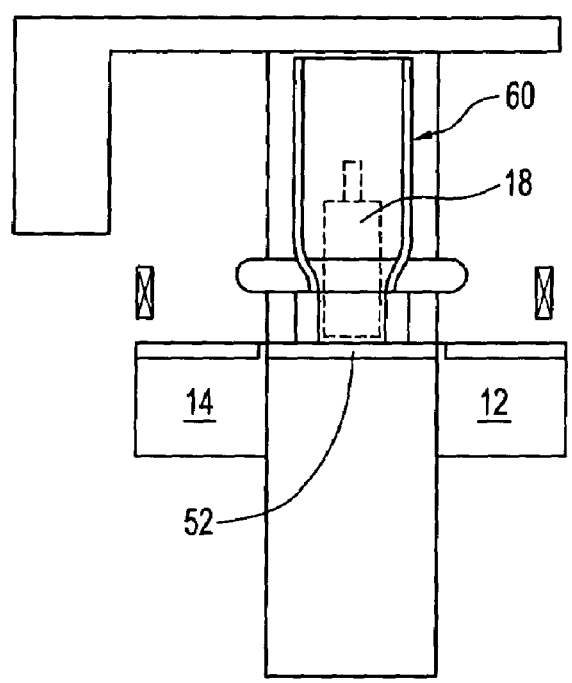
FIG. 9 is a front elevational view of the lane changer showing the shuttle in a second position.
Figure 10:
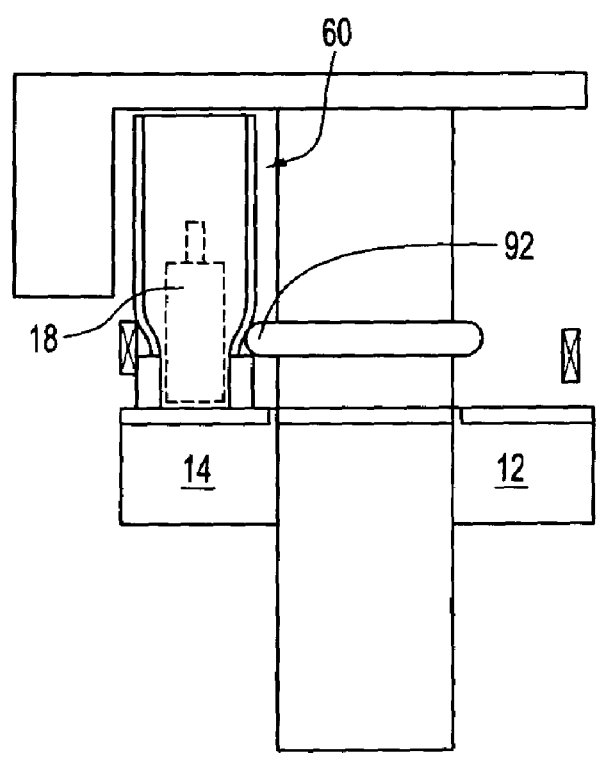
FIG. 10 is a front elevational view of the lane changer showing the shuttle in a third position.

Command module 24 will then transmit instructions to positioning assembly 100 to release carrier 18, to permit movement to the a "hold" position "D" in land changing device 22. As shown in FIG. 6, the "hold" position locates shuttle 60 slightly inwardly from the lane of conveyor 12, so that blade 82 directs the carrier between arms 68 and 70, and into contact with stop 90. If carrier 18 is to be diverted to conveyor 14, then command module 24 will instruct lane changer 22 to move shuttle 60 across platform 52, as shown in FIG. 7, to the "release" position "E" on conveyor 14. The release position "E" locates carrier 18 on conveyor 14 so that it bypasses stop 92, to permit the carrier to proceed downstream, as shown in FIG. 8. As the carrier leaves lane changer 22 it will pass exit sensor 88 at position "F", which will confirm that the desired action has occurred.

In the alternative, if carrier 18 is to be released along conveyor 12 rather than diverted to conveyor 14, then shuttle 60 will be instructed to move outwardly from the "hold" position to the "release" position. This movement will cause carrier 18 to be moved outwardly beyond the end of stop 90, permitting the carrier to proceed downstream on conveyor 12. As the carrier leaves lane changer 22, it will pass exit sensor 88 at position "G", which will confirm that the desired action has been taken.

This same sequence of actions (except for the step of stopping at positioning assembly 100) occurs with a carrier 18 that approaches queue 20 along conveyor 14, with the same options of releasing the carrier on the same conveyor, or diverting the carrier to conveyor 12 at lane changer 22.

Whereas the invention has been shown and described in connection with the preferred embodiment thereof, many modifications, substitutions and additions may be made which are within the intended broad scope of the appended claims.

What is claimed is:

1. A transfer and positioning apparatus for positioning a specimen container carried in a specimen carrier at a predetermined position along a first conveyor of a dual conveyor track and for transferring the carrier between the two conveyors, the track of the type having first and second parallel, spaced apart conveyors with upper surfaces within a single plane, the conveyors operable in the same longitudinal direction, the transfer and positioning apparatus comprising:

a positioning assembly mounted between the conveyors at a predetermined processing location, for positioning a specimen container within a carrier at a reference location;

a lane changer mounted between the conveyors downstream of the positioning assembly, for selectively transferring a specimen carrier between the first and second conveyors; and a command module with a processor electrically connected to and programmed to operate the positioning assembly and the lane changer;

said positioning assembly including:

an assembly housing mounted between the conveyors;

a retractable shaft in a forward wall of the assembly housing, operable between an extended position extending over the first conveyor to prevent downstream movement of a carrier on the first conveyor, and a retracted position permitting downstream movement of a carrier;

a pair of first and second gripper arms operably mounted within the assembly housing and operable for simultaneous movement between an open position and a closed position, the open position having the first arm located downstream of the reference location and the second arm located upstream of the reference location with both arms spaced from a path of a specimen container on the conveyor to permit carriers with specimen containers to move past the gripper arms, the closed position having the first and second gripper arms in contact with a specimen container and locating the specimen container at the reference location; and a motor in said housing connected to the arms and operable to selective move the arms between the open and closed positions;

said motor electrically connected to the command module processor and responsive to operate the gripper arms in response to instructions transmitted from the processor;

said lane changer comprising:

a frame connected to the track downstream of the positioning assembly, for supporting an operable shuttle;

a shuttle operably connected to the frame to move transversely between the conveyors and generally perpendicular to the movement of specimen carriers on the conveyors;

a first stop member on said frame, projecting partially over the first conveyor;

a second stop member on said frame, projecting partially over the second conveyor;

said shuttle having a pair of parallel arms spaced apart a distance to receive a specimen carrier therebetween;

said shuttle operable to a first "hold" position with the shuttle arms located such that a specimen carrier therebetween is in contact with the first stop member, to thereby prevent downstream movement of a carrier on the first conveyor;

said shuttle operable to a first "release" position with the shuttle arms located such that a specimen carrier therebetween bypasses the first stop member and is moved downstream through the shuttle arms on the first conveyor;

said shuttle operable to a second "release" position with the shuttle arms located such that a specimen carrier therebetween bypasses the second stop member and is moved downstream through the shuttle arms on the second conveyor; and a drive assembly on the frame electrically connected to the command module processor, for selectively moving the shuttle among the first "hold" position, the first "release" position and the second "release" position; and said command module processor programmed according to predetermined rules and guidelines for the processing of specimens within containers on carriers on the track; and said command module processor programmed to provide operating instructions to the lane changer and positioning assembly.

2. The transfer and positioning apparatus of claim 1, wherein said positioning assembly further includes a sensor adjacent the retractable shaft to detect the presence of a carrier at said retractable shaft, said sensor electronically connected to the command module for transmitting detection information thereto.

3. The transfer and positioning apparatus of claim 1, wherein said positioning assembly further includes a scanner in said housing oriented to scan a specimen carrier restrained by the retractable shaft, to collect identification data therefrom, said scanner electrically connected to the command module and adapted to transmit identification data to the command module.

4. The transfer and positioning apparatus of claim 1, wherein said positioning assembly gripper arms are pivotally mounted at rearward ends thereof for movement of forward ends through a generally horizontal plane.

5. The transfer and positioning apparatus of claim 4, wherein said positioning assembly gripper arms are operably interconnected at their rearward ends for simultaneous movement of the forward ends in opposing directions.

6. The transfer and positioning apparatus of claim 1, wherein the forward ends of the gripper arms each have a contact surface for contacting the specimen container.

7. The transfer and positioning apparatus of claim 6, wherein each contact surface has a shape that will position the container along a longitudinal axis of the first conveyor track when the arms are moved to the closed position.

8. The transfer and positioning apparatus of claim 1, wherein said shuttle is operable to a second "hold" position with the shuttle arms located such that a specimen carrier therebetween is in contact with the second stop member to thereby prevent downstream movement of a carrier on the second conveyor, and wherein said drive assembly additionally selectively moves the shuttle to the second "hold" position.

9. The transfer and positioning apparatus of claim 8, wherein said lane changer frame further includes a first sensor located to detect the presence of a carrier within the arms of the shuttle in the first "hold" position, said sensor electronically connected to the command module for transmitting detection information thereto.

10. The transfer and positioning apparatus of claim 9, wherein said lane changer frame further includes a second sensor located to detect the presence of a carrier within the arms of the shuttle in the second "hold" position, said sensor electronically connected to the command module for transmitting detection information thereto.

11. The transfer and positioning apparatus of claim 10, wherein said frame further includes a first exit sensor located downstream of the first lane changer sensor along the first conveyor, to detect the presence of a carrier that has exited the arms of the shuttle in the first "release" position, said sensor electronically connected to the command module for transmitting detection information thereto.

12. The transfer and positioning apparatus of claim 11, wherein said lane changer frame further includes a second exit sensor located downstream of the second lane changer sensor along the second conveyor, to detect the presence of a carrier that has exited the arms of the shuttle in the second "release" position, said sensor electronically connected to the command module for transmitting detection information thereto.

13. The transfer and positioning apparatus of claim 1, further comprising a queue positioned upstream of said positioning assembly and mounted between said conveyors, for selectively restraining specimen carriers on the conveyors upstream of the positioning assembly and lane changer and selectively releasing a specimen carrier from one of said conveyors in response to instructions from the command module, said queue electronically connected to the command module to receive instructions therefrom.

14. The transfer and positioning apparatus of claim 13, wherein said queue includes:

a housing mounted between the conveyors;

a first retractable shaft projecting from a downstream end of the queue housing and over the first conveyor, to restrain a specimen carrier from movement along the first conveyor when extended;

a motor in said queue housing connected to said queue first shaft for selectively extending and retracting said shaft, said motor electrically connected to the command module and responsive to instructions from the command module;

a second retractable shaft projecting from a downstream end of the queue housing and over the second conveyor, to restrain a specimen carrier from movement along the second conveyor when extended;

said motor in the queue housing connected to said second shaft for selectively extending and retracting said shaft;

a first queue sensor adjacent said first queue shaft for detecting the presence of a specimen carrier restrained by the first queue shaft;

said first queue sensor electrically connected to the command module and adapted to transmit detection data to the command module; and a second queue sensor adjacent said second queue shaft for detecting the presence of a specimen carrier restrained by the second queue shaft;

said second queue sensor electrically connected to the command module and adapted to transmit detection data to the command module.

15. The transfer and positioning apparatus of claim 14, wherein said queue first and second shafts are connected together, such that the retraction of one shaft causes the extension of the other, whereby no more than one specimen carrier may be released at a time by the queue.

16. The transfer and positioning apparatus of claim 15, wherein said queue further includes:

a first queue scanner adjacent said first queue shaft for scanning a specimen carrier restrained by the first queue shaft, to collect identification data therefrom;

said first queue scanner electrically connected to the command module and adapted to transmit identification data to the command module; and a second queue scanner adjacent said second queue shaft for scanning a specimen carrier restrained by the second shaft, to collect identification data therefrom;

said second queue scanner electrically connected to the command module and adapted to transmit identification data to the command module.

17. The transfer and positioning apparatus of claim 16, wherein said first queue scanner is activated to scan in response to the detection of the presence of a specimen carrier by the first queue sensor, and wherein the second queue scanner is activated to scan in response to the detection of the presence of a specimen carrier by the second queue sensor.

18. The transfer and positioning apparatus of claim 17 wherein said queue further includes:

a third retractable shaft projecting from an upstream end of the queue housing and over the first conveyor, to restrain a specimen carrier from movement along the first conveyor when extended;

a second queue motor in said queue housing connected to said third queue shaft for selectively extending and retracting said shaft, said second queue motor electrically connected to the command module and responsive to instructions from the command module;

a fourth retractable shaft projecting from an upstream end of the queue housing and over the second conveyor, to restrain a specimen carrier from movement along the second conveyor when extended;

said second queue motor connected to said fourth queue shaft for selectively extending and retracting said shaft;

a third queue sensor adjacent said third queue shaft for detecting the presence of a specimen carrier restrained by the third queue shaft;

said third queue sensor electrically connected to the command module and adapted to transmit detection data to the command module; and a fourth queue sensor adjacent said fourth shaft for detecting the presence of a specimen carrier restrained by the fourth queue shaft;

said fourth queue sensor electrically connected to the command module and adapted to transmit detection data to the command module.

\* \* \* \* \*